United States Patent [19]

Marhold

[11] Patent Number: 4,581,466

[45] Date of Patent: Apr. 8, 1986

[54] PROCESS FOR THE PREPARATION OF BENZO-FUSED, TETRACHLORINATED HETEROCYCLIC COMPOUNDS

[75] Inventor: Albrecht Marhold, Leverkusen, Fed. Rep. of Germany

[73] Assignee: Bayer Aktiengesellschaft, Leverkusen, Fed. Rep. of Germany

[21] Appl. No.: 715,565

[22] Filed: Mar. 25, 1985

[30] Foreign Application Priority Data

Mar. 31, 1984 [DE] Fed. Rep. of Germany ....... 3412079

[51] Int. Cl.⁴ .................. C07D 319/02; C07D 319/14
[52] U.S. Cl. ..................................... 549/359; 549/362
[58] Field of Search ............................... 549/362, 359

[56] References Cited

U.S. PATENT DOCUMENTS 3,749,677 7/1973 Maulding ........................... 549/362

4,348,323 9/1982 Fuchs et al. ........................ 549/362

FOREIGN PATENT DOCUMENTS 3329126 2/1985 Fed. Rep. of Germany ...... 549/362

OTHER PUBLICATIONS

Maulding et al, Journ. Org. Chem., 37(9), 1972, pp. 1458–1459.

*Primary Examiner*—Ethel G. Love
*Attorney, Agent, or Firm*—Sprung, Horn, Kramer & Woods

[57] ABSTRACT

Benzo-fused, tetrachlorinated heterocyclic compounds are prepared by first reacting pyrocatechol or a pyrocatechol derivative with tetrachloroethylene carbonate, with the addition of a tertiary amine, and then adding phosphorus pentachloride, without intermediate isolation.

13 Claims, No Drawings

PROCESS FOR THE PREPARATION OF BENZO-FUSED, TETRACHLORINATED HETEROCYCLIC COMPOUNDS

A process has been found for the preparation of benzo-fused, tetrachlorinated heterocyclic compounds of the formula

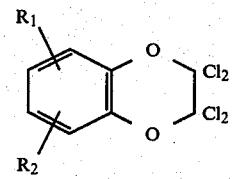

in which $R_1$ and $R_2$ independently of one another represent hydrogen, fluorine, chlorine, bromine, COCl, $CO_2CH_3$, cyanide, alkyl, nitro, $SO_2Cl$, $SO_2F$, $OCF_3$, $SCF_3$, $CF_3$, $CCl_3$, $CBr_3$, phenyl, substituted phenyl, O-alkyl, O-aryl, S-alkyl or S-aryl, or $R_1$ and $R_2$ together represent

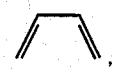

which is characterized in that pyrocatechol or a pyrocatechol derivative of the formula

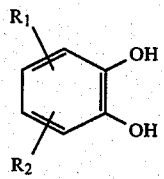

in which $R_1$ and $R_2$ have the abovementioned meaning, is first brought together with tetrachloroethylene carbonate and a catalytic amount of a tertiary amine in any desired sequence at 50° to 100° C. in the presence of an inert solvent, and, when the reaction which takes place has ended, at least 2 moles of phosphorus pentachloride are added to the reaction mixture per mole of compound of the formula (II) employed, and the reaction mixture is then left at an elevated temperature for a further period.

If $R_1$ and/or $R_2$ in the formulae (I) and (II) represent substituted phenyl, they can be, for example, phenyl radicals with 6 to 10 C atoms, which can be substituted by nitro, fluorine, chlorine, bromine, cyanide, $C_1$- to $C_4$-alkyl, $SO_2Cl$, $SO_2F$, $OCF_3$, $SCF_3$, $CF_3$, $CCl_3$, $CBr_3$, O-$C_1$- to $C_4$-alkyl or S-$C_1$- to $C_4$-alkyl.

If $R_1$ and/or $R_2$ in the formulae (I) and (II) represent alkyl, O-alkyl and/or S-alkyl, the particular alkyl radical can contain, for example, 1 to 4 C atoms.

If $R_1$ and/or $R_2$ in the formulae (I) and (II) represent O-aryl and/or S-aryl, the particular aryl radical can contain, for example, 6 to 10 C. atoms.

Preferably, $R_1$ and $R_2$ in the formulae (I) and (II) independently of one another represent hydrogen, fluorine,, chlorine, methyl, nitro or phenyl, or $R_1$ and $R_2$ together represent

Particularly preferably, in the formulae (I) and (II), $R_1$ represents hydrogen and $R_2$ represents hydrogen, nitro, methyl or phenyl, or $R_1$ and $R_2$ together represent

The compounds of the formula (II) to be employed in the process according to the invention are either commercially available or are accessible in a simple manner, for example in accordance with Houben-Weyl, Methoden der organischen Chemie (Methods of Organic Chemistry), volume VI/1c, page 327 et seq. (1976), or by processes analogous to these.

The tetrachloroethylene carbonate to be employed in the process according to the invention can be obtained, for example, by chlorination of ethylene carbonate in accordance with U.S. Pat. No. 2,815,287.

Tetrachloroethylene carbonate is preferably employed in a molar excess in relation to the compound of the formula (II) employed, for example in an amount of 1.01 to 2 moles per mole of the compound of the formula (II). It is particularly preferable to use 1.1 to 1.5 moles of tetrachloroethylene carbonate per mole of the compound of the formula (II).

Examples of possible tertiary amines are trimethylamine, triethylamine, dimethylphenylamine, pyridine, lutidine, 4-dimethylaminopyridine, collidine, quinoline, 1,8-diazabicyclo-[5,4,0]-undec-7-ene (=DBU) and 1,5-diazabicyclo-[4,3,0]-non-5-ene (=DBN). Pyridine and pyridine-like amines are preferred. The tertiary amine can be employed, for example, in amounts of 0.1 to 5 g. per 100 g of tetrachloroethylene carbonate.

Suitable solvents for the process according to the invention are, for example, chlorinated hydrocarbons, in particular those with a boiling point above 60° C., such as chloroform, carbon tetrachloride, chlorobenzene or dichlorobenzene.

The compound of the formula (II), the tetrachloroethylene carbonate, the tertiary amine and the solvent can be brought together in any desired sequence. For example, it is possible to take the compound of the formula (II) and then to add the tertiary amine, dissolved in a solvent, and subsequently to add the tetrachloroethylene carbonate. It is also possible to take the tertiary amine together with the solvent and then to slowly add the tetrachloroethylene carbonate, allow the reaction which starts to subside and subsequently to add the compound of the formula (II). It is also possible to take the compound of the formula (II) together with the solvent, to add the tetrachloroethylene carbonate and finally to add the tertiary amine.

The reaction of the compound of the formula (II) with tetrachloroethylene carbonate or with the mixture present after the reaction of tetrachloroethylene carbonate with the tertiary amine is carried out at 50° to 100° C. This temperature is preferably 65° to 85° C. This reaction has ended when the evolution of hydrogen chloride ceases, which is in general the case after about 2 to 10 hours.

It is an essential feature of the present invention that no isolation of the reaction products is now undertaken, but at least 2 moles of phosphorus pentachloride per mole of compound of the formula (II) employed are added directly to the reaction mixture present. In general, larger amounts of phosphorus pentachloride cause no trouble. From economic considerations, 2 to 3 moles of phosphorus pentachloride are preferably employed per mole of compound of the formula (II) used.

After the addition of the phosphorus pentachloride, the reaction mixture is kept at 60° to 150° C. for a further 0.5 to 10 hours. Reaction times of 2 to 6 hours and temperatures of 65° to 120° C. are preferred here.

The mixture then present can be worked up, for example, by first distilling off the phosphorus oxychloride formed and the solvent, during which any excess phosphorus pentachloride present sublimes, and then subjecting the remaining residue to fractional distillation in vacuo. If necessary, the resulting compounds of the formula (I) can be further purified by recrystallisation. Such a recrystallisation can be carried out, for example, with hydrocarbons, such as cyclohexane, toluene or xylene, or alcohols, such as methanol or ethanol.

The compounds of the formula (I) are accessible in a simple manner and in good yields and selectivities by the process according to the invention.

The compounds of the formula (I) are useful products from which anilines can be prepared, for example, by fluorination which is known per se with hydrogen fluoride (see, for example, German Offenlegungsschrift No. 33 29 126) and, if appropriate, subsequent nitration and reduction, and from these anilines, compounds which, according to German Offenlegungsschriften Nos. 3,023,328 and 3,223,505, are insecticides are accessible by reaction with acylisocyanates.

The following examples illustrate the process according to the invention, without limiting it in any way.

EXAMPLES

Example 1

400 ml of dry chlorobenzene and 2 ml of pyridine were taken and were warmed to 65° to 70° C. 320 g of tetrachloroethylene carbonate were then added dropwise. Evolution of gas started immediately. After 3 hours, the evolution of gas at 75° to 80° C. had ended. Thereafter, 110 g of pyrocatechol were introduced via a substance valve, vigorous evolution of hydrogen chloride starting immediately. The temperature was kept at 80° C. When the addition had ended, the mixture was subsequently stirred at 80° C. for a further 3 hours. The evolution of gas had then stopped and, from analysis by gas chromatography, all the pyrocatechol had reacted. 480 g of phosphorus pentachloride were now added and the mixture was heated at the reflux temperature for 4 hours. Thereafter, the phosphorus oxychloride and chlorobenzene were distilled off, excess phosphorus pentachloride subliming. Distillation of the residue which remained gave 23 g of first runnings with a boiling point of 95° to 118° C. under 8 mbar, 220 g of tetrachlorobenzodioxene with a boiling point of 118°–130° C. under 8 mbar and 19 g of a residue which was not investigated more closely.

Example 2

440 g of pyrocatechol and 3 ml of pyridine were taken in 1,200 ml of chlorobenzene. 1,000 g of tetrachloroethylene carbonate were then added dropwise at 75° C. During the reaction at 75° to 80° C., 0.5 ml of pyridine was metered in each hour. When the evolution of hydrogen chloride had ended, 1,900 g of phosphorus pentachloride were added and the mixture was heated at the reflux temperature for 5 hours. It was then subjected to fractional distillation. 585 g of tetrachlorobenzodioxene were obtained.

Examples 3 to 6

The procedure followed was as in Example 2, but pyrocatechol derivatives were used instead of pyrocatechol. The results can be seen from Table 1.

TABLE 1

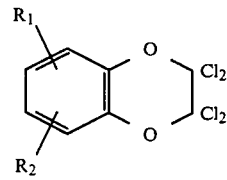

| Example No. | Reaction product | Yield (% of theory) | Boiling point or melting point (°C.) |
|---|---|---|---|
| 3 | 6-nitro | 74 | 81–82 (melting point) |
| 4 | 5-methyl | 70 | 158–162/20 mbar (boiling point) |
| 5 | 6-phenyl | 78 | 115–117 (melting point) |
| 6 | 6,7-  | 83 | 175–178 (melting point) |

What is claimed is:

1. A process for the preparation of a benzofused, tetrachlorinated heterocyclic compound of the formula

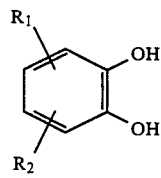

wherein $R_1$ and $R_2$ independently of one another represent hydrogen fluorine, chlorine, bromine, COCl, $CO_2CH_3$, cyanide, alkyl, nitro, $SO_2Cl$, $SO_2F$, $OCF_3$, $SCF_3$, $CF_3$, $CCl_3$, $CBr_3$, phenyl, substituted phenyl, O-alkyl, O-aryl, S-alkyl or S-aryl, or $R_1$ and $R_2$ together represent

//\\, which comprises contacting a pyrocatechol compound of the formula wherein $R_1$ and $R_2$ have the above-mentioned meaning with tetrachloroethylene carbonate and a catalytic amount of a tertiary amine at 50° to 100° C. in the presence of an inert solvent and, when the reaction is substantially complete, contacting the resultant reaction product with at least 2 moles of phosphorus pentachloride per mole of pyrocatechol compound and permitting said phosphorus pentachloride to react with the reaction product of said pyrocatechol and said tetrachloroethylene carbonate at an elevated temperature.

2. A process according to claim 1 wherein $R_1$ and $R_2$ independently of one another represent hydrogen, fluorine, chlorine, methyl, nitro or phenyl or $R_1$ and $R_2$ together represent

3. A process according to claim 1 wherein 1.01 to 2 moles of tetrachloroethylene carbonate are employed per mole of pyrocatechol compound.

4. A process according to claim 1 wherein said amine is trimethylamine, triethylamine, dimethylphenylamine, pyridine, lutidine, 4-dimethylaminopyridine, collidine, quinoline, 1,8-diazabicyclo-[5,4,0]-undec-7-ene or 1,5-diazabicyclo-[4,3,0]-non-5-ene.

5. A process according to claim 1 wherein said amine is employed in an amount of 0.1 to 5 grams per 100 grams of tetrachloroethylene carbonate.

6. A process according to claim 5 wherein said amine is employed in an amount of 0.1 to 5 grams per 100 grams of tetrachloroethylene carbonate.

7. A process according to claim 1 wherein said solvent is a chlorinated hydrocarbon whose boiling point is above 60° C.

8. A process according to claim 1 wherein said phosphorus pentachloride is employed in an amount of 2 to 3 moles per mole of pyrocatechol compound.

9. A process according to claim 1 wherein said phosphorus pentachloride reacts with the reaction product of said pyrocatechol compound and said tetrachloroethylene carbonate at a temperature of 60° to 150° C. for 0.5 to 10 hours.

10. A process according to claim 9 wherein the reaction of said phosphorus pentachloride is carried at 65° to 120° C. for 2 to 6 hours after addition of said phosphorus pentachloride.

11. A process according to claim 1 wherein after the reaction with phosphorus pentachloride is substantially complete, the phosphorus oxychloride formed as the result of said reaction and the solvent are distilled off and the residue which remains is then subjected to a fractional distillation in vacuo.

12. A process according to claim 1 wherein the process is carried out without isolation of the tetrachloroethylene carbonate/pyrocatechol compound reaction product.

13. A process according to claim 12 wherein said phosphorus pentachloride is added to the reaction mixture resulting from reaction of said pyrocatechol compound and said tetrachloroethylene carbonate.

* * * * *